(12) United States Patent
Bontigao et al.

(10) Patent No.: US 10,500,316 B2
(45) Date of Patent: Dec. 10, 2019

(54) ODOR NEUTRALIZING MASK INSERT

(71) Applicants: Marie Angela Bontigao, Torrance, CA (US); David Emery, Torrance, CA (US)

(72) Inventors: Marie Angela Bontigao, Torrance, CA (US); David Emery, Torrance, CA (US)

( * ) Notice: Subject to any disclaimer, the term of this patent is extended or adjusted under 35 U.S.C. 154(b) by 634 days.

(21) Appl. No.: 15/199,940

(22) Filed: Jun. 30, 2016

(65) Prior Publication Data
US 2017/0021063 A1 Jan. 26, 2017

Related U.S. Application Data

(60) Provisional application No. 62/194,876, filed on Jul. 21, 2015.

(51) Int. Cl.
| | | |
|---|---|---|
| *A61L 31/14* | (2006.01) | |
| *A61L 31/02* | (2006.01) | |
| *A61L 31/00* | (2006.01) | |
| *A61L 9/014* | (2006.01) | |
| *A61L 9/16* | (2006.01) | |
| *A61L 9/00* | (2006.01) | |
| *A41D 13/11* | (2006.01) | |

(52) U.S. Cl.
CPC .......... *A61L 31/14* (2013.01); *A41D 13/1192* (2013.01); *A61L 9/00* (2013.01); *A61L 9/014* (2013.01); *A61L 9/16* (2013.01); *A61L 31/005* (2013.01); *A61L 31/024* (2013.01); *A61L 31/028* (2013.01); *A61L 2209/22* (2013.01); *A61L 2300/404* (2013.01)

(58) Field of Classification Search
CPC ... A61L 31/14; A61L 9/00; A61L 9/16; A61L 9/014; A61L 31/005; A61L 31/024; A61L 31/028; A61L 2209/22; A61L 2300/404; A41D 13/1192; A41D 13/1209; A41D 13/1184; A41D 13/1176; A41D 13/1161; A41D 13/11; A62B 17/04; A62B 18/02; A62B 18/025; A62B 23/02; A62B 23/025; A62B 23/00; B01D 2259/4541
USPC ........................................................ 128/863
See application file for complete search history.

(56) References Cited

U.S. PATENT DOCUMENTS

| | | | | |
|---|---|---|---|---|
| 4,951,664 A | * | 8/1990 | Niemeyer ............ | A62B 18/025 128/205.27 |
| 5,467,765 A | * | 11/1995 | Maturaporn ....... | A41D 13/1115 128/206.12 |

(Continued)

*Primary Examiner* — Tarla R Patel
(74) *Attorney, Agent, or Firm* — Payam Moradian

(57) ABSTRACT

An air-permeable guard adapted to attach to a covering, the air permeable guard comprising a plurality of layers attached together to create one or more compartments. The guard further comprises at least one agent stored in the one or more compartments wherein the at least one agent may be a counteracting agent, a masking agent or a disinfectant agent. The masking agent may be coffee, oil and self encapsulated oil beadlet. The counteracting agent may be activated charcoal, sodium bicarbonate, zeolite, diatomaceous earth, silica gel and bentonite clay. The disinfectant agent may be a water based coating containing a cationic siloxane. In another embodiment of the invention the compartments may store the agents in a portion of the guard that is adapted to come in contact with the wearer's nostrils.

14 Claims, 4 Drawing Sheets

(56) References Cited

U.S. PATENT DOCUMENTS

| | | | | |
|---|---|---|---|---|
| 5,697,105 A * | 12/1997 | White | ............... | A41D 13/1146 |
| | | | | 128/205.27 |
| 5,706,804 A * | 1/1998 | Baumann | ........... | A41D 13/1115 |
| | | | | 128/206.12 |
| 6,070,578 A * | 6/2000 | Baughman | ......... | A41D 13/1192 |
| | | | | 128/205.27 |
| 6,338,340 B1 * | 1/2002 | Finch | ................... | A62B 18/084 |
| | | | | 128/205.27 |
| 2003/0111075 A1 * | 6/2003 | Wen | ...................... | A62B 18/02 |
| | | | | 128/201.22 |
| 2004/0231671 A1 * | 11/2004 | Begum | ............. | A41D 13/1161 |
| | | | | 128/206.12 |
| 2008/0092909 A1 * | 4/2008 | Hahne | ................ | A41D 13/1192 |
| | | | | 128/863 |
| 2012/0111344 A1 * | 5/2012 | Goranov | ........... | A41D 13/1115 |
| | | | | 128/863 |

* cited by examiner

ODOR NEUTRALIZING MASK INSERT

CROSS REFERENCE TO RELATED APPLICATIONS

This application claims priority to U.S. provisional patent application Ser. No. 62/194,876 filed on Jul. 21, 2015, the contents of which are hereby incorporated by reference in their entirety into the present application.

FIELD OF THE INVENTION

This invention relates to a device for use in blocking or reducing bad odors that make it difficult to complete a task, perform work duties, and/or in other situations where odor negatively impacts quality of life.

BACKGROUND OF THE ART

People are exposed to odors and smells that can have a strong and negative effect on their ability to perform a task, work, or even in the quality of their daily life. Although there are many masks (e.g., surgical masks) on the market, they often only serve to block liquid droplets, pathogens or airborne particles but not deal with odors. Sometimes, a deluxe model of the mask may be available that does deal with odor, either through filtering the odor particles, blocking them, or masking them with some other chemical scent, but they are often cost prohibitive even as disposable items (as single units, let alone the multiples required for daily use). Sometimes an approved mask (e.g., by a government body or professional organization) is provided by an employer but fails to address the odor problem so a person needs something that can work in conjunction with the already provided and required work mask.

BACKGROUND OF THE INVENTION

There are several instances where a person is exposed to unpleasant odors or strong smells that can induce nausea or make the person so uncomfortable that it is impossible to work, perform a task, or maintain quality of life.

There are three main areas: performing work duties, completing a task and, in general, living life comfortably.

I. Performing Work Duties:

In the context of caring for patients, the care-giver, typically a nurse or doctor, is often exposed to unpleasant odors which make performing the work difficult or even impossible. People in the healthcare field note that the following conditions or situations (not an exhaustive list) create odors that make it exceptionally difficult to work: pressure sores, burning hair/flesh, bowel movements, abscesses, gastrointestinal bleeding, gangrene, homeless patients (layers of unwashed clothing, matted hair, etc.), pseudomonas. Many who work with these conditions on a regular basis have a number of imperfect ways to deal with the odors and make it possible to complete their work duties. Some place alcohol wipes between their face and the hospital-provided mask, but that leaves their face wet and the alcohol can irritate the sensitive tissue in the sinuses and throat. Some use lip balm, an oil, or mentholated vapor rub inside the mask or on their lip, which can cover the odor but leaves a residue on the skin. Some may breathe through their mouth, which is only partially effective. Some wear face shields to try and block the odor.

Other professions deal with issues of odor in the workplace including those in waste (both garbage and portable toilets), crime scene cleaning, tanneries, various types of farming, slaughterhouse worker, roadkill remover, morticians, lift pump/sewer cleaners and engineers.

II. Completing a Task:

The above examples deal with situations a worker may face daily. Other situations at home or work arise on a task by task basis such as taking out the garbage, taking the garbage to the dumpster, painting, doing a home repair, changing an especially dirty diaper, cleaning if a pet or member of the family has vomited, bled or defecated over an area. Sometimes a family member may need to care for an elderly or otherwise sick/bed-bound individual and that care can render the non-professional (who lacks experience dealing with certain smells) nauseous or distressed. In these situations a specialized and expensive air filtration mask may solve the problem, but many people resort to covering their mouths and noses with their hand, a shirt, a bandanna, or some other method to try and make the situation bearable long enough to complete the task.

III. Living Life Comfortably:

Many of the above tasks may fall under this category, but there are certain instances where one may feel sick or need to block/replace an odor. For instance, many expectant mothers face problems with morning sickness. Often, a strong smell or unpleasant odor can make them sick to their stomachs and vomit. Another example may be a person who suffers headaches or is just generally affected by strong smells and needs something to improve the air entering their body. Other short-term situations may arise like home renovation (painting a room or replacing a wall), home repair (sewer, sink, bathroom, toilet repair), the cigarette/cigar/pipe smoke from someone nearby temporarily entering your home on an irregular basis. In the past, this situation has been dealt with in one or more of the following manners: masks or other blocking mechanisms, expensive filters, chemicals to cover scents, special liners, or inserts that require specialized/vented clothing. Therefore, a continued need exists for a way to block, reduce, and cover odors naturally, safely, cheaply, and in a way that complements existing purchased or provided materials.

SUMMARY OF THE INVENTION

The invention comprises an air-permeable guard that is inserted between the face and another object such as a mask or other covering like a bandanna folded to cover mouth that acts to block, adsorb, counteract, or replace odors before the air enters the nose or mouth.

It is an object of the invention to provide an air-permeable guard composed of paper, cloth, plastic, melt-blown fibers or a mixture of those material in one or more layers of those materials that is placed between the face and the mask or object being used to try and block the odor. The typical embodiment may have two to six layers but other embodiments are specifically contemplated and within the scope of this invention. In many instances the guard will be disposable and include the improvement of being able to be reused one or more times. Additionally, another embodiment is made to be more durable and last longer. Together the different layers result in different compartments in which substances may be stored. Regardless of the version, the invention also comprises a combination of substances that primarily serve to absorb and adsorb odors (counteracting agents) and that may have a substance to cover and provide a pleasant scent for the wearer (masking agent), and that may also have an agent to perform anti-fungal/bacterial/microbial functions (e.g., a disinfectant agent). A counteracting agent, as that term is used in this specification, is a substance that serves to absorb and adsorb odors. A masking agent, as that term is used in this specification, is a substance that provides a pleasant scent. A disinfectant agent, as that term is used in this specification, is a substance that inhibits the growth of fungi, bacteria or microbes. The layers are joined either by stitching or by other methods such as with an adhesive or with a heat pressure seal. Between the two layers closest to the face is a substance such as coffee, an oil or self encapsulated oil beadlet, or any other substance known to one skilled in the art that produces a pleasant odor and/or that makes the air inhaled more acceptable. Between the layers closest to the mask side (furthest from the face) is a substance to absorb and/or adsorb the odor such as activated charcoal, sodium bicarbonate, zeolite, diatomaceous earth, silica gel, bentonite clay, or other natural and non-toxic substances. The terms activated carbon, active carbon, and activated charcoal as used in this specification are interchangeable terms. Further, any amount of the substances may be used for either the compartment housing the counteracting agents or for the compartment housing the substances that produce a pleasant odor. The only limitation is based on the size of the compartments created by the different layers.

Although the preferred embodiment contains five layers, additional layers may be added in order to include additional absorption substances. Additionally, fewer layers may be used (as few as 2) if the substances are mixed together and depending on whether the guard is needed to protect the user from infections and liquid droplets. In general, the preferred method is to separate the masking agent from the counteracting agent, causing the effects of both to be more pronounced and increase the life and effectiveness of the guard. The simplest form the guard can take is as a single layer. The masking and counteracting agents can be mixed into a wet slurry, applied to a single layer, and allowed to dry onto a single layer. The guard may also have a method to slightly adhere it to the mask side so that it does not shift or move substantially after being placed. Placing it on the mask side means that it does not leave a substance or residue on the skin.

The shape of the guard also changes depending on the primary usage. For general use when used in conjunction with a shirt, bandana, or other cover, the shape is a square or rectangle so that it easily covers an area of the face sufficient to block and adsorb odors as air passes through it. For use with traditional square or rectangular shaped masks, disposable or not, the guard is square or rectangle, but sized smaller so that it fits comfortably inside the mask. For masks that are of a more rounded nature, a guard that is circular or ovoid in shape will best fit inside the mask and cover an area of the face sufficient to be effective. Since most masks are of uniform size and shape, a couple of sizes will fit a majority of masks currently used. Additionally, the shape of the guard may be designed to match a person's nose and mouth resulting in a nontraditional shape but which may fit naturally between a person's face and a mask or other object that is used to cover the face.

DETAILED DESCRIPTION OF SOME EMBODIMENTS OF THE INVENTION

The preferred embodiment of the guard is one made from a combination of five layers made of paper, plastic, and fibers that serve to block airborne liquids as well as feel soft against the skin, while leaving the person using the device with a pleasant scent.

Figure 1:
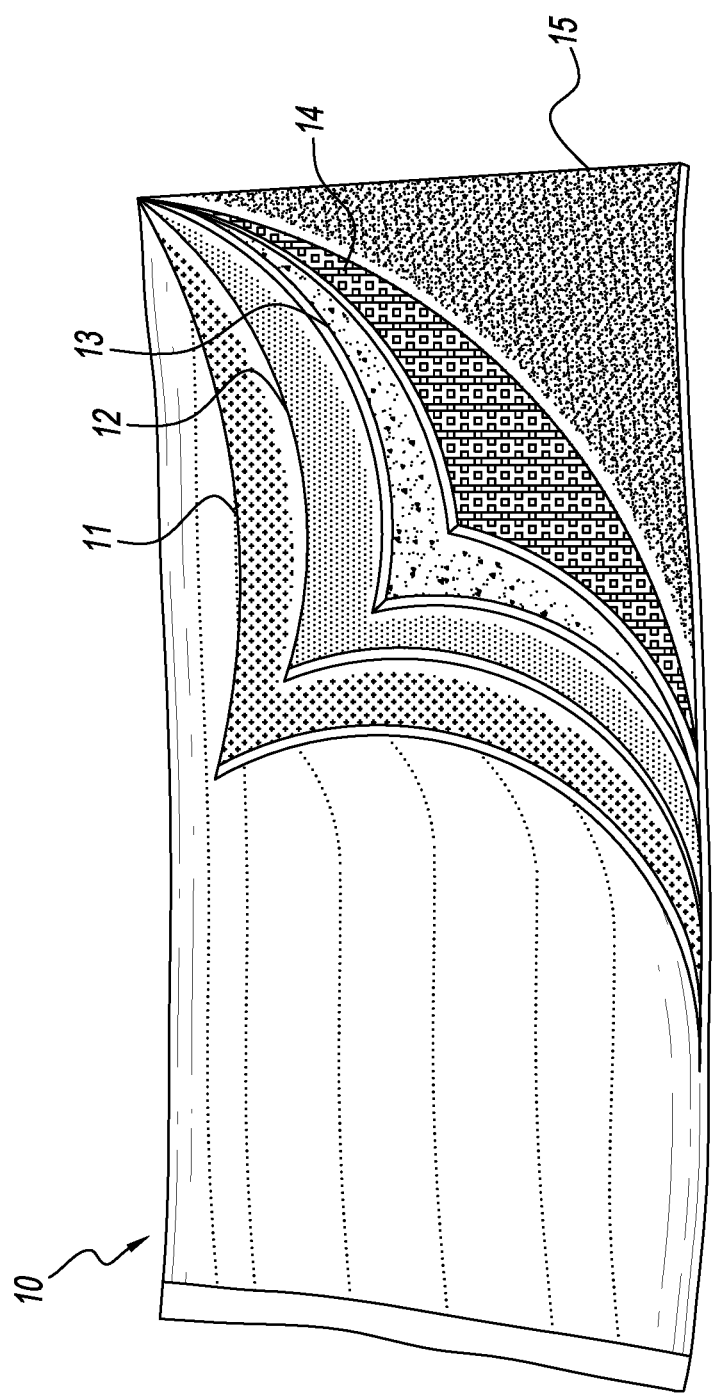
FIG. 1 shows an embodiment of the present invention comprising five layers and four compartments between the layers.

The layers may be bonded by heat seal or stitching. As shown in in FIG. 1, the guard 10 comprises a first layer 11 that touches the face. Between the second and third layers, 12 and 13 respectively, is between 0.5 and 2.5 grams of ground coffee, though it can be more or less depending on the strength of the scent needed and found useful or tolerable by the individual using the guard. Between the third and fourth layers, 13 and 14 respectively is between 0.1 and 2.5 grams of activated charcoal and 0.1 to 5 grams of sodium bicarbonate, though these amounts may be changed depending on the need of the individual using the guard, the strength of the odor, and the expected length of time the guard will be used. In general, the ratio of sodium bicarbonate to activated charcoal is approximately 2-to-1. The fifth and final layer 15 touches the mask or other object covering the user's face. The outer side of 15 contains a slight adhesive needed to hold the guard in place. On the mask side is a light adhesive covered in removable sections so that the guard may stick slightly to avoid shifting after being placed and also be used multiple times before being disposed.

Figure 2:
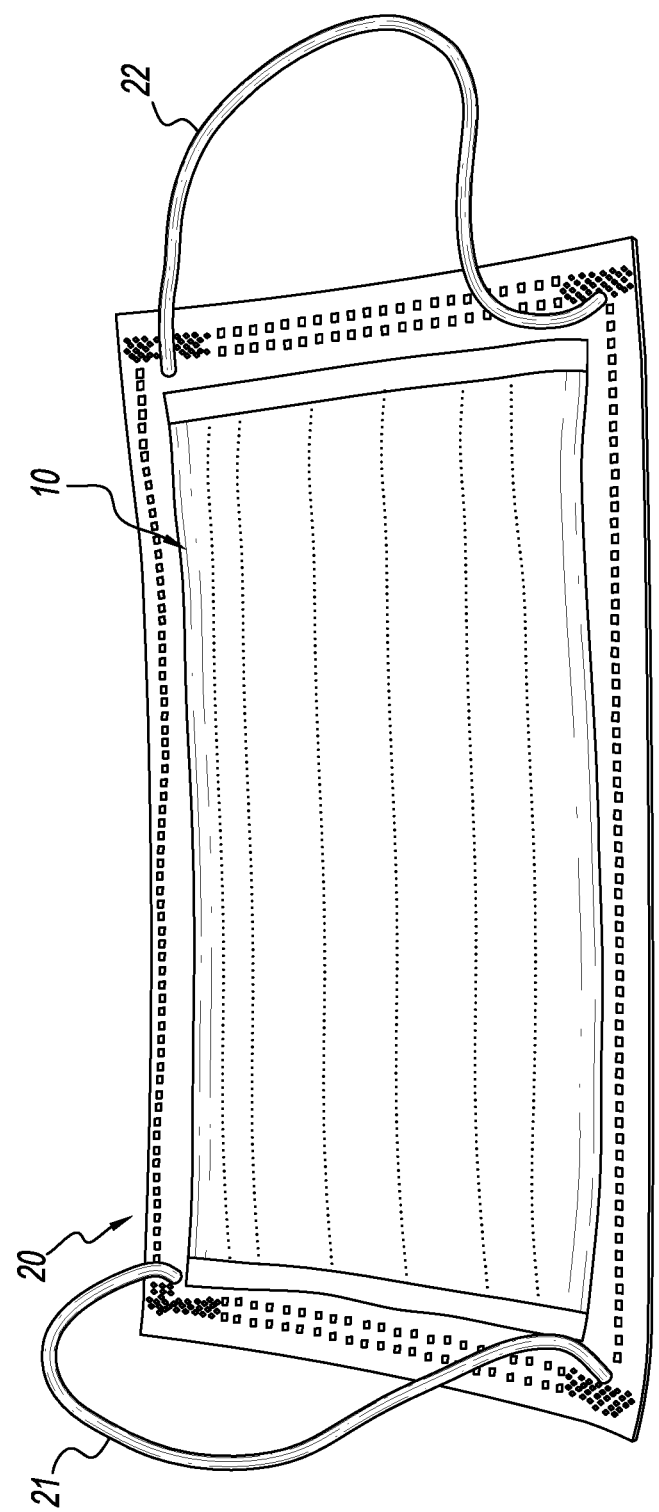
FIG. 2 shows an embodiment of the present invention attached to a standard surgical mask.

As shown in FIG. 2, the guard 10 is attached to a standard surgical mask 20. The surgical mask 20 comprises two straps, a strap for the left ear 21 and one for the right ear 22. When a user wears the mask with the guard attached to the mask, the first layer of the guard comes in contact with the user and the last layer is in contact with the surgical mask.

Figure 3:
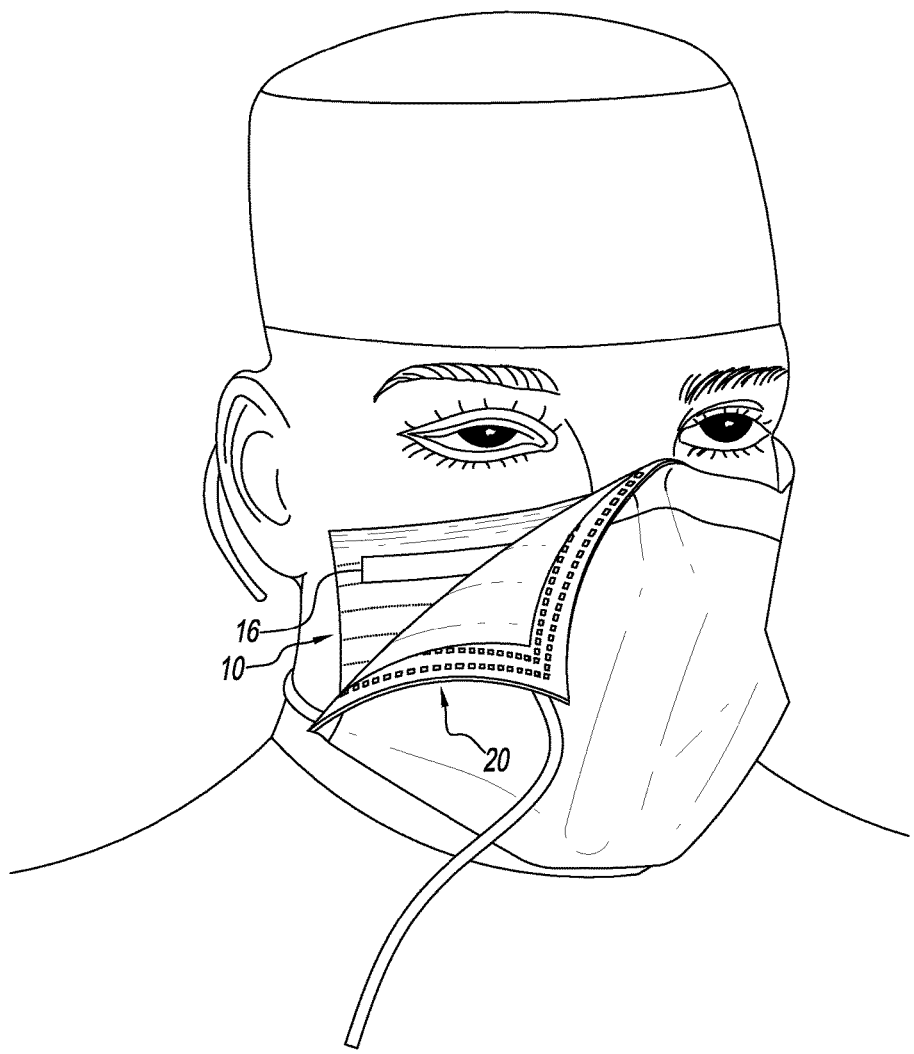
FIG. 3 shows a perspective view of an embodiment of the present invention in between the user's face and the surgical mask as the mask is peeled away.

As shown in FIG. 3, the guard 10 is on the user's face with the surgical mask 20 peeled away. On the last layer of the guard 10 is an adhesive strip 16 that is used to connect the guard 10 to the mask 20.

In one embodiment, the shape of the guard is a rectangle approximately 15 centimeters lengthwise and 7.5 centimeters tall. However, other dimensions are contemplated and also within the scope of this invention.

Activated charcoal may be used and stored within the guard because it is porous and adsorbs odors. A single gram of activated charcoal has a surface area between 500 $m^2$ and 1500 $m^2$. Sodium bicarbonate (baking soda) may be used as a base and neutralizes acidic odors. Coffee ground may be used because odor particles adhere to it and it also provides a pleasant scent that masks most odors.

Figure 4:
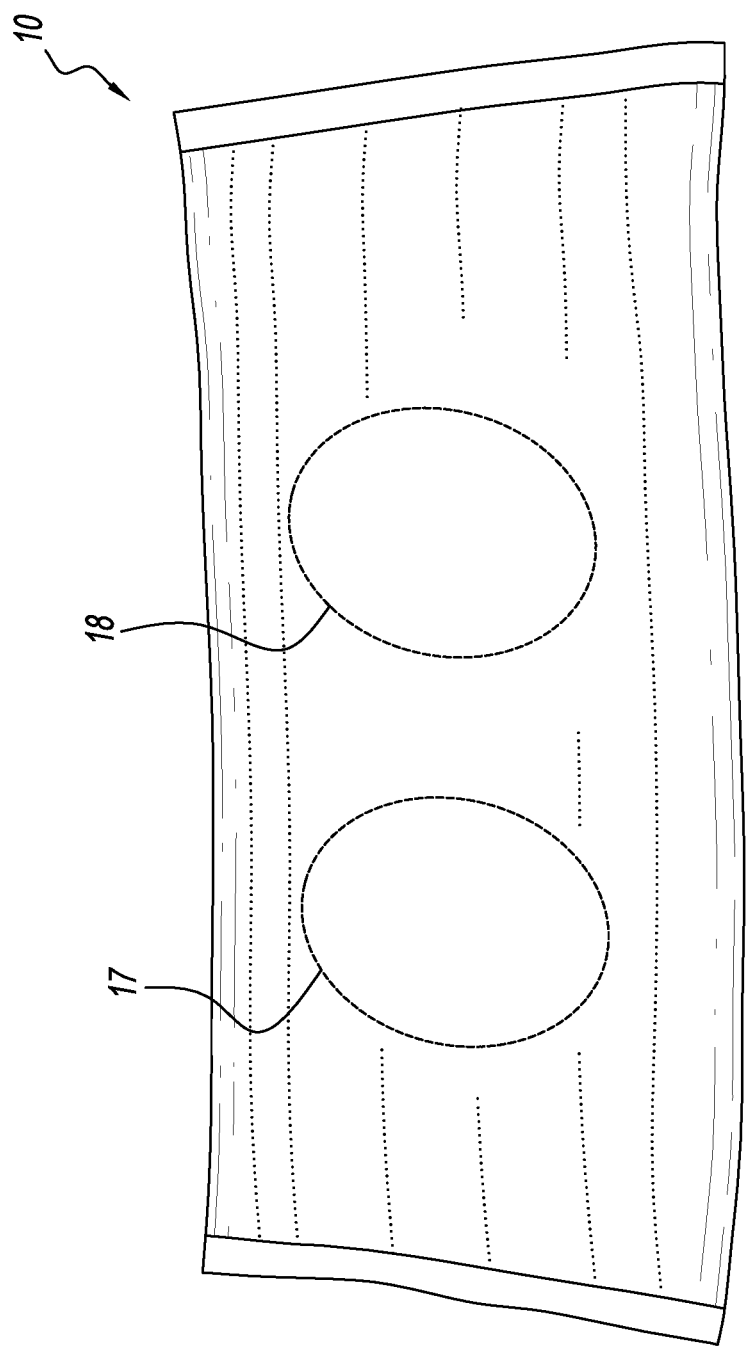
FIG. 4 shows another embodiment of the present invention wherein the substances stored between the layers are confined to two areas in the middle of the guard.

In another embodiment of this invention, specially placed compartments exist between the different layers. As one example of this embodiment and as shown in FIG. 4 the first two layers are stitched to form two compartments 17 and 18 in which ground coffee or other pleasant smelling substances are placed. The position of these two compartments allow for these substances to be placed close to a user's nostrils. The compartments may be created by stitching the first two layers in the center in addition to the stitching at the corners. One advantage of these compartments is to provide the substance in a compact and direct manner to a user's nostril. In another embodiment of the present invention the specially placed compartments (e.g., near the center by the user's nostrils) exist between all the layers of the guard and not just between the first two layers.

In another embodiment of the present invention oil or a self encapsulated essential oil beadlet may be used. This can replace or be used in conjunction with the coffee ground. Essential Oil beadlets are currently available from companies such as doTERRA and Ameo. These beadlets contain essential oils in a small sphere which can be broken or punctured by applying pressure at which point oil is released. For example, a cardamom essential oil beadlet is made from cardamom seeds which have been distilled into an essential oil. Other non-limiting examples of essential oils include eucalyptus, cinnamon bark, ginger, clove, lemon, juniper berry, peppermint and spearmint. The essential oil may be held in a gelatin matrix. One advantage of these beadlets is that a plurality of them may be contained within the guard and whenever the user wishes to "activate" them he can break a beadlet. In this manner the user may break several beadlets to intensify the amount of oil or he may conserve the beadlets and break one before each time he wears the guard.

In another embodiment of this invention the disinfectant agent used is a water based coating that contains a cationic siloxane. One such agent is commercially available as BIOSAFE® and may be covered by U.S. Pat. Nos. 6,572,926 and 6,146,688. This agent is not metabolized by a microbe's cells. Rather this agent may create a network of electrically charged microscopic spikes on the surface of a cell. These spikes may "pop" the microbe's cell walls, effectively neutralizing it.

Although this present invention is described with a preferred embodiment and includes details related to other embodiments of the same idea, workers skilled in the design will recognize that changes may be made in form and detail without departing from the spirit and scope of the invention.

What is claimed is:

1. An air-permeable guard adapted to attach to a covering, the air permeable guard comprising:
   a plurality of layers attached, together to create one or more compartments;
   at least one agent stored in a first compartment holding one agent adapted to fit a left nostril and a second compartment holding same or different agent adapted to fit a right nostril; and wherein the at least one agent may be a counteracting agent, a masking agent or a disinfectant agent.

2. The air-permeable guard of claim 1 wherein the covering is a surgical mask and wherein the air permeable guard is further adapted to fit a human face.

3. The air-permeable guard of claim 2 wherein the plurality of layers are comprised of one or more material selected from the group consisting of paper, cloth, plastic, or fiber.

4. The air-permeable guard of claim 3 wherein the plurality of layers are attached together with an adhesive.

5. The air-permeable guard of claim 3 wherein the plurality of layers are attached together by bond heating the plurality of layers.

6. The air-permeable guard of claim 3 wherein the plurality of layers are attached together by stitching the plurality of layers.

7. The air-permeable guard of claim 6 wherein the plurality of layers comprises three or more layers wherein the three or more layers form two or more compartments.

8. The air-permeable guard of claim 7 wherein a masking agent is stored in a first compartment and a counteracting agent is stored in the second compartment.

9. The air-permeable guard of claim 8 wherein the masking agent is coffee.

10. The air-permeable guard of claim 6 wherein the plurality of layers comprises five layers, the first layer adapted to fit a human face, the second and third layers adapted to store between 0.5 and 2.5 grams of ground coffee, the third and fourth layers adapted to store between 0.1 and 2.5 grams of activated charcoal and 0.1 to 5 grams of sodium bicarbonate, and wherein the plurality of layers are rectangular in shape.

11. The air-permeable guard of claim 1 wherein the counteracting agent is selected from the group consisting of, sodium bicarbonate, zeolite, diatomaceous earth, silica gel and bentonite clay.

12. The air-permeable guard of claim 11 wherein a disinfectant agent is stored in one of the two or more compartments and wherein the disinfectant agent is a water based coating containing a cationic siloxane.

13. The air-permeable guard of claim 1, wherein the first and second portions of the first compartment are stitched closed.

14. The air-permeable guard of claim 13 therein the guard is attached to the surgical mask with an adhesive.

\* \* \* \* \*